United States Patent [19]
Napierkowski et al.

[11] Patent Number: 5,906,800
[45] Date of Patent: May 25, 1999

[54] STEAM DELIVERY SYSTEM FOR A DECONTAMINATION APPARATUS

[75] Inventors: Susan Mary Napierkowski, Erie; Kenneth John Klobusnik; Francis John Zelina, both of Lake City, all of Pa.

[73] Assignee: Steris Corporation, Mentor, Ohio

[21] Appl. No.: 08/833,245

[22] Filed: Apr. 4, 1997

[51] Int. Cl.⁶ .............................. A61L 2/06; F22B 27/00; F22B 29/06

[52] U.S. Cl. ............................ 422/298; 422/307; 122/40; 392/398; 392/399

[58] Field of Search ............................ 422/26, 110, 111, 422/108, 305, 307, 298, 299; 122/40; 392/386, 394, 398, 399

[56] References Cited

U.S. PATENT DOCUMENTS

| | | |
|---|---|---|
| 2,045,479 | 6/1936 | Luff . |
| 2,288,247 | 6/1942 | Kunstorff . |
| 3,836,458 | 9/1974 | Wallis et al. . |
| 4,108,601 | 8/1978 | Wolff ........................................ 422/295 |
| 4,203,947 | 5/1980 | Young et al. . |
| 4,601,300 | 7/1986 | Sundheimer . |
| 4,999,165 | 3/1991 | Calabra et al. ...................... 422/295 X |
| 5,290,511 | 3/1994 | Newman .............................. 422/298 X |

FOREIGN PATENT DOCUMENTS

| | | |
|---|---|---|
| 0350515 A1 | 1/1990 | European Pat. Off. . |
| 3219141 A1 | 11/1983 | Germany . |
| 2055289 | 3/1981 | United Kingdom . |
| 2131695 | 6/1984 | United Kingdom ................... 422/298 |
| WO 96/41099 | 12/1996 | WIPO . |

*Primary Examiner*—E. Leigh McKane
*Attorney, Agent, or Firm*—Fay, Sharpe, Beall, Fagan, Minnich & McKee, LLP

[57] ABSTRACT

A steam sterilizer device having a steam generation system is disclosed. The steam generation system has a fluid connection to a water source (1) to provide water to a venturi apparatus (27) for the selective creation of a vacuum in a sterilization chamber (71). A fluid connection to a particle filter (33) and a reverse osmosis filter (37) is also provided and water passed through the filters is delivered by a metering pump (53) to a steam generating apparatus (59) which in turn supplies steam to a the chamber (71). The chamber (71) is provided with a discharge conduit including a mixing chamber (31) and a split tubing air break (131).

10 Claims, 2 Drawing Sheets

STEAM DELIVERY SYSTEM FOR A DECONTAMINATION APPARATUS

BACKGROUND OF THE INVENTION

The present invention relates generally to the decontamination art. It finds particular application in the sterilizing and disinfecting apparatus typically employed to clean, sterilize and disinfect medical, veterinary, mortuary, and laboratory instruments and equipment and will be described with particular reference thereto. More particularly, the present invention finds application in a steam sterilization apparatus which requires its own source of steam. It will be appreciated, however, that the invention may be applicable to a wide variety of apparatus used in sanitizing and disinfecting.

Medical, dental, surgical, veterinary, and laboratory equipment and instruments are often sterilized by exposure to steam or steam in combination with other vapors. Typically, an apparatus is provided which isolates the equipment and instruments in a high pressure, high temperature steam environment for a sufficient period of time to complete cleaning and/or sterilization. For example, the steam autoclave devices of the type described in U.S. Pat. Nos. 4,193,818; 4,226,642; and 4,601,300, herein incorporated by reference, demonstrate steam autoclaves of the type generally related to the present invention.

In most steam sterilizer applications, the apparatus is utilized in an institutional setting wherein "house" steam is available from the physical facilities of the building in which it is located. In certain instances, however, it is desirable to have a sterilizer containing its own system for generation of steam. For example, in smaller medical or laboratory facilities and in most lesser developed regions of the world, house steam is not available. In fact, in instances where house steam is temporarily unavailable, it may even be desirable to have a steam sterilization device that provides steam source via a self-contained steam generation system.

Historically, in self-generating steam sterilizers, a small boiler has been provided within the sterilization unit or as a separate stand alone device to provide steam. Typically, these boilers have been an immersion heat system wherein a heating element is immersed in a large water containing reservoir.

The inventive steam delivery system is envisioned as suited to be used in combination with a boiler type steam generator of the type described in U.S. Pat. No. 4,767,502, herein incorporated by reference. Nonetheless, while the present inventive steam delivery system can be used in conjunction with a traditional stand alone boiler, a preferred embodiment of the invention is to combine the present inventive steam delivery system with a flash steam generator of the type described in U.S. Ser. No. 08/485,736 filed Jun. 7, 1995, herein incorporated by reference.

In an attempt to provide a self-contained steam generation system for a sterilization device, a variety of important requirements must be accomplished. More specifically, the system must be suited to handling of the variety of contaminants and mineral contents found in tap water throughout the United States, and in fact, throughout the world. Similarly, a variety of governmental regulations exist concerning, for example, water temperatures, discharge piping arrangements, and other safety constraints. To accomplish this goal, sterilization units having a self-contained system for steam generation have been highly complicated and expensive. The present invention provides an inventive and significant improvement over the units previously in existence.

SUMMARY OF THE INVENTION

Steam sterilizers use steam as a medium to sterilize a load of medical or laboratory goods. Steam must be supplied to and removed from a chamber in a cycle that is appropriate for the load being sterilized. This may involve alternating vacuum to remove the air entrapped in the load and a controlled exposure to pressurized, saturated steam at an appropriate temperature. Although some installations provide saturated steam for the sterilizer, some applications require steam to be generated by the sterilizer device itself. This invention identifies a unique fluid delivery system design for steam sterilizers.

In accordance with one aspect of the present invention, a steam sterilization device having a chamber for receiving articles to be decontaminated is provided. The sterilization device includes a steam generation system which is constructed to include a fluid inlet suitable for mating with an outside water source. The fluid inlet is connected by a conduit to a venturi apparatus which itself is connected via a conduit to a sterilization chamber, allowing a vacuum to be selectively created within the sterilization chamber. In addition, the venturi apparatus is connected by a conduit to a port to pull a vacuum on the seal of the chamber door. This type of arrangement is particularly described in the U.S. Pat. No. 4,228,135, herein incorporated by reference.

The inlet is also connected by a conduit to a first particulate filter which in turn is connected to a second reverse osmosis filter. A conduit links the reverse osmosis filter to a fluid reservoir equipped with a sensor to monitor the fluid level. A metering pump is connected via a conduit to the fluid reservoir and to a steam generating apparatus which in turn is connected via conduit to the sterilization chamber. The chamber includes an outlet to a discharge element having overlapping, yet disconnected sections of tubing.

In a particularly preferred form of the invention, the conduit and requisite valving and connections of the system are comprised of stainless steel to allow pure steam to be generated.

Particularly preferred inventive elements of the above-described system include the utilization of a metering pump in combination with a flash steam generator, preferably in combination with a filter mechanism including a particulate filter and a reverse osmosis filter. An additional inventive aspect of the present system is the utilization of a mixing tank having a first connection to an outside water source and a second connection to the exhaust outlet of the sterilization chamber, allowing cooling on demand of the effluent from the chamber. A further inventive element of the subject system is the split tubing air break forming a feature of the discharge conduit.

Still further advantages of the present invention will become apparent to those of ordinary skill in the art upon reading and understanding the following detailed description of the invention.

BRIEF DESCRIPTION OF THE DRAWINGS

The invention may take form in various components and arrangements of components, and in various steps and arrangements of steps. The drawings are only for purposes of illustrating a preferred embodiment and are not to be considered as limiting the invention.

DETAILED DESCRIPTION OF THE INVENTION

Reference will now be made in detail to the present preferred embodiment of the invention, an example of which is illustrated in the accompanying drawings. While the invention will be described in connection with a preferred embodiment, it will be understood that it is not intended to limit the invention to that embodiment. On the contrary, it is intended to cover all alternatives, modifications and equivalents as may be included within the spirit and scope of the invention defined by the appended claims.

Figure 1:
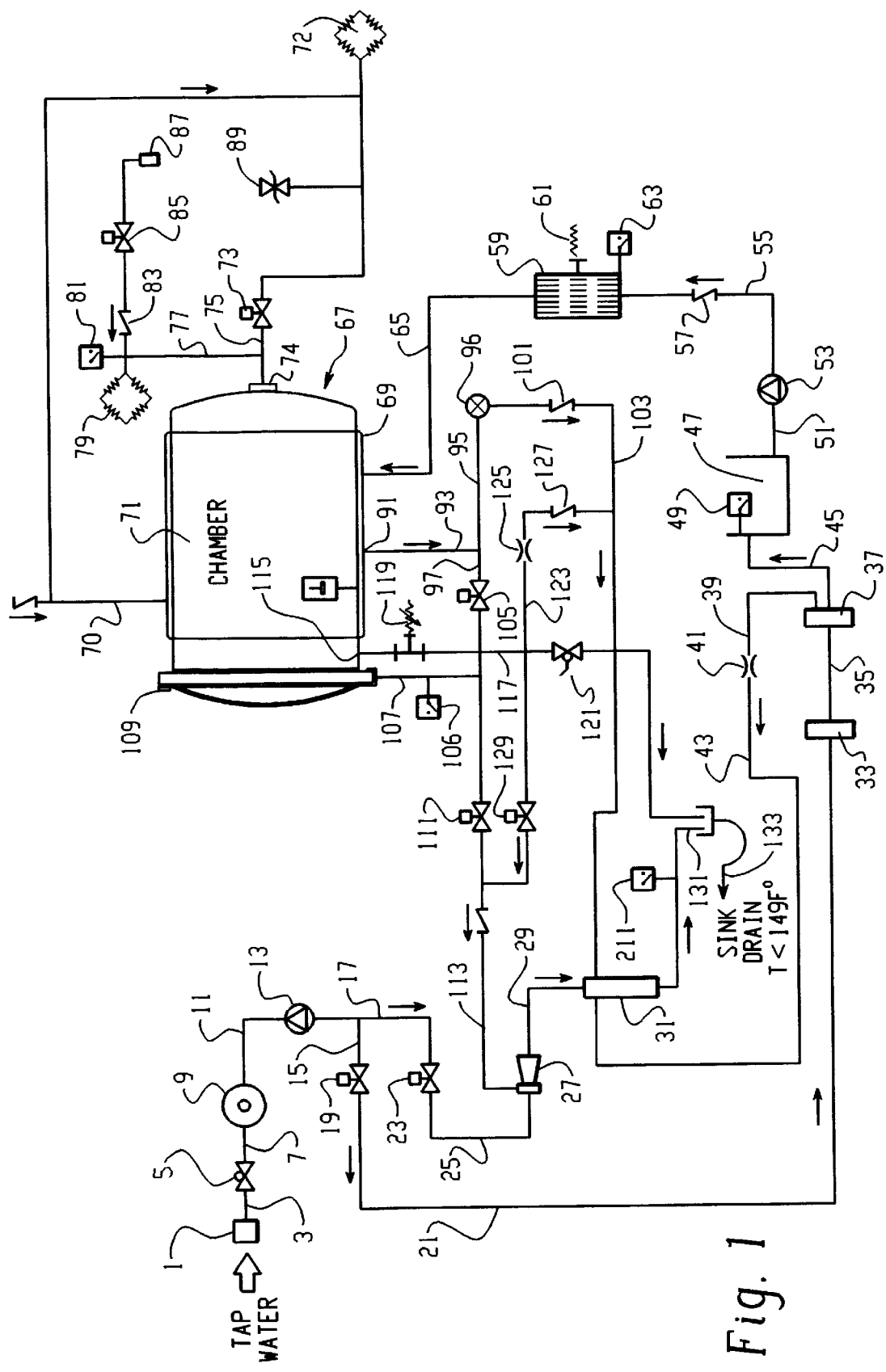
FIG. 1 is a schematic illustration of the inventive steam generation system.

Referring now to FIG. 1, it will be seen that the inventive sterilizer having a self-contained steam generation system is comprised of a connection 1 to a water source. Water entering the connection 1 passes through conduit 3 and through a water supply cut off valve 5. Water continues through a conduit 7 passing through a confirmation strainer water regulator 9, a conduit 11 and into a pump 13. Preferably, the pump 13 is of an electric or rotary type and provides at least 80 pounds per square inch of pressurized water. The pump 13 provides water to a pair of split conduits 15 and 17. Water passing through the conduit 15 passes through valve 19 and then to a conduit 21 which feeds the filtration system and eventually provides steam to the autoclave.

Water passing through conduit 17 is controlled by a valve 23 to maintain a proper flow of water to a conduit 25 and therefore a venturi device 27. Preferably the venturi device is of a type available from Schutte & Koerting, i.e. model 835-X004J. Water passing through the venturi device 27 enters a conduit 29 and passes into a mixing tank 31. Referring again to the steam generation path of the system via the conduit 21, water passes through a particle filter 33, through a conduit 35, and through a reverse osmosis filter 37. Water rejected by the reverse osmosis filter is passed through a conduit 39 containing a flow restrictor 41, into a conduit 43, and eventually enters the mixing tank 31.

Water which passes through the reverse osmosis filter 37 enters a conduit 45 and passes into a reservoir 47, equipped with a water level sensor 49. Water from the reservoir 47 passes through a conduit 51 to a metering pump 53, which provides precise quantities of water via a conduit 55 equipped with a check or one-way valve 57 to a flash steam generator 59. Preferably the metering pump is of a positive displacement style, for example, model no. 210 available from March Manufacturing.

The flash generator 59 may be the type described in U.S. Ser. No. 08/485,736, herein incorporated by reference, wherein a solid carbon steel block is equipped with a plurality of heating members and water passes through the device. As illustrated, a resistive temperature detector 61 and an over temperature switch 63 are provided. Steam exits the generator 59 and passes through a conduit 65 to a sterilization apparatus 67. The steam enters a jacket 69 surrounding a chamber 71.

Steam exits the jacket 69 via a conduit 70 which allows pressure monitoring by a transducer 72. A safety valve 89 is provided for as a necessary release for the jacket steam system. Steam passes through a valve 73 and enters the rear of the sterilization chamber 71 through an inlet 74 via conduit 75. To maintain appropriate pressures in the sterilization chamber 71, a pressure monitoring system is attached to the conduit 75. Particularly, a conduit 77 is provided with a chamber pressure transducer 79, pressure chamber switch 81, a check valve 83, valve 85 and an air inlet with filter 87.

An additional outlet 91 to the jacket 69 provides steam to a conduit 93 forming a "t" connection with conduits 95 and 97. The conduit 95 is equipped with a trap 96 which is preferably a thermostatic type of trap to allow condensation in the jacket to be discharged through check valve 101 into a conduit 103 and eventually into the mixing tank 31. The conduit 97 includes valve 105 which is used to provide steam, as controlled by pressure switch 106, via a conduit 107 to a door seal 109. When a steaming cycle is completed, valve 105 is closed, and a valve 111 is opened allowing a vacuum to be drawn by the venturi device 27 via conduit 113.

The chamber 71 is evacuated via outlet 115 passing to conduit 117 which includes an resistive temperature detector 119. The conduit 117 includes a first connection to an exhaust hand valve 121 which is normally kept closed but can be utilized as required to provide immediate drainage via an air break 131 to drain 133.

In normal operation, a small flow of steam will travel through a conduit 123, passing through a restricted flow point 125, through check valve 127 and eventually into the mixing tank 31. This continuous minimal flow of steam provides an accurate read for the chamber RTD 119.

A valve 129 provides a standard discharge route for steam during cycling or upon completion of sterilization where an opening of the valve 129 permits steam to flow into conduit 113, the water ejector device 27, and eventually to the mixing tank 31 and out to via an air break 131 to a floor drain or sink style P-trap drain 133.

In general, the sterilization device will be provided with a microprocessor monitoring the sensors and to control valving and other controlled elements of the system. An exemplary software/microprocessor control for the subject inventive steam generation system is described in U.S. patent application Ser. No. 08/832,648, entitled STEAM STERILIZATION APPARATUS AND CONTROL SYSTEM, filed concurrently to the subject application, the disclosure of which is herein incorporated by reference.

Figure 2:
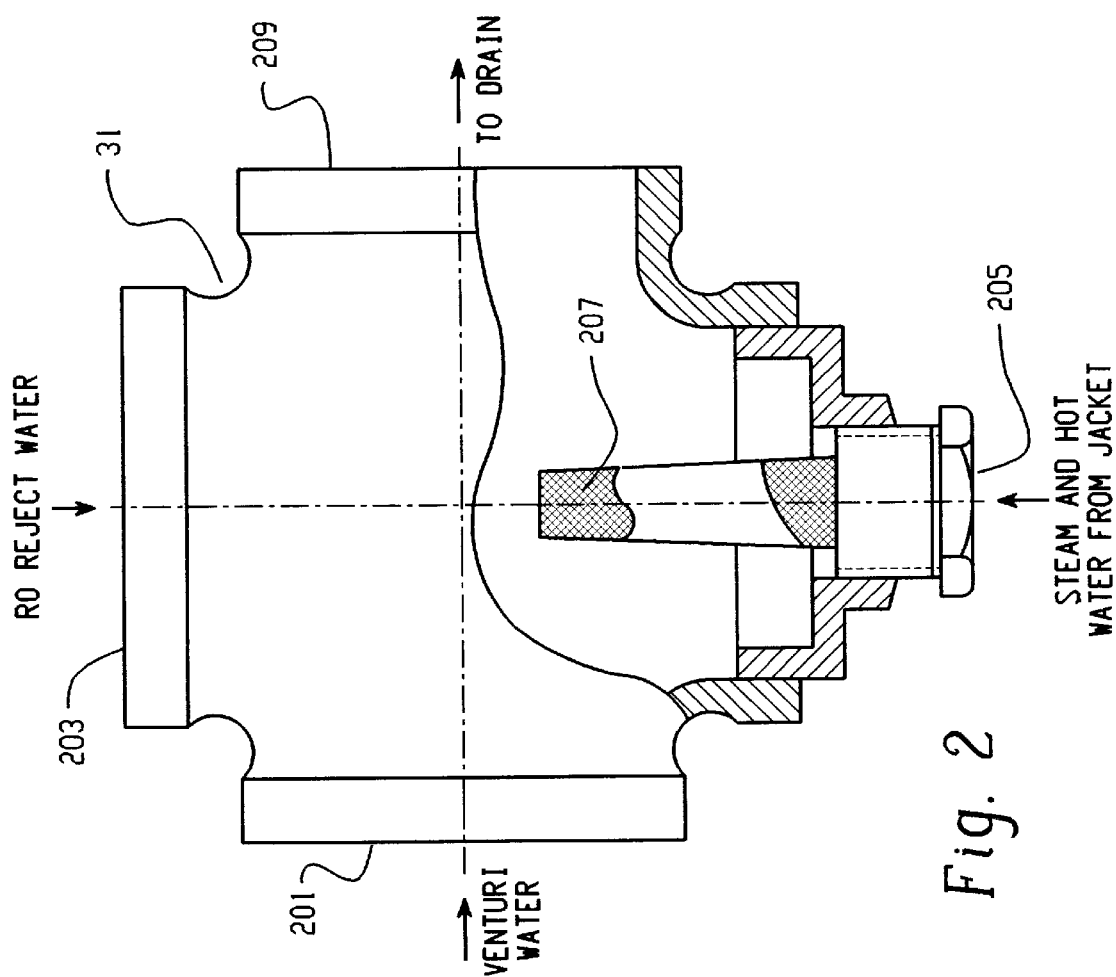
FIG. 2 is a cross sectional view of the inventive mixing tank.

Referring now to FIG. 2, the inventive discharge mixing tank 31 is depicted in detail. As illustrated, effluent from the seal and chamber of the sterilization device enters from the venturi at inlet 201, reverse osmosis filter reject water enters at 203, and water/steam from the jacket/chamber enters at 205. Discharge water from the jacket/chamber is sparged into the mixing tank through a screened nozzle 207 which is preferably located at the base of the mixing tank 31. Water exits the mixing tank 31 via outlet 209 and is discharged to an external drain. This inventive design provides for the elimination of waste water in a manner where a temperature sensor 211 on the drain allows venturi device water (i.e. cool water) as controlled by valve 23 to be added to the mixing tank as necessary to obtain an appropriate water temperature for discharge such as less than 140° F.

Figure 3:
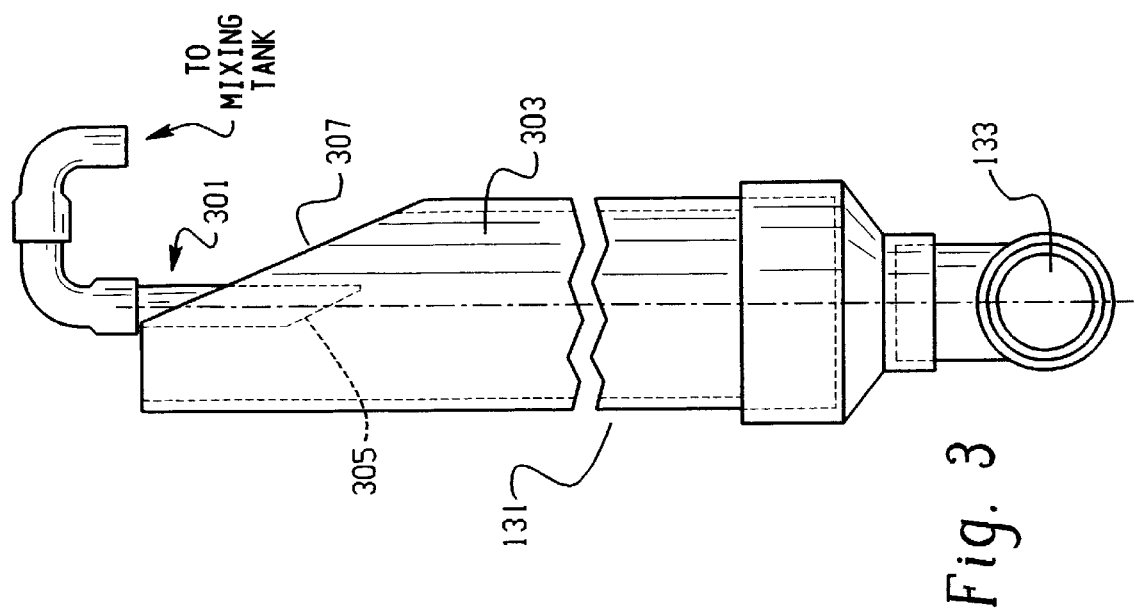
FIG. 3 is a perspective view, partially in cross section, of the inventive discharge piping assembly.

Referring now to FIG. 3, discharge water during an emergency via the valve 121 or as is more typical, from mixing tank 31, is passed through the air break 131. The air break 131 include a top element 301 and a larger diameter bottom element 303. The top element 301 penetrates slightly into the bottom element 303 and each is provided with a facing beveled surface 305 and 307 respectively. As will be recognized, the air break prevents back-up water from a drain from reaching the sterilization unit.

Thus is it apparent that there has been provided in accordance with the invention, a sterilization device steam generation system that fully satisfies the objects, aims, and advantages set forth above. While the invention is described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the dependent claims.

We claim:

1. A steam sterilizer device including a steam generation system, said system comprised of a fluid connection to a water source, said fluid connection in communication with a venturi apparatus which is connected to a sterilization chamber to selectively create a vacuum, said fluid connection also providing water to a first particle filter and a second reverse osmosis filter, said filters in fluid communication with a metering pump which provides water to a steam generating apparatus comprised of a metallic block having at least one fluid conduit passing from a first to a second end and a plurality of elongated heating elements disposed in bores in said block adjacent and generally parallel to said fluid conduit which in turn supplies steam to said chamber, a chamber exhaust conduit in fluid communication with a mixing tank, said mixing tank further including a fluid communication with an outside water source, at least one of said filters, and a discharge conduit, said discharge conduit including an air break.

2. The device of claim 1 including a reservoir to accept water from said reverse osmosis filter.

3. The device of claim 1 including a fluid connection between said venturi apparatus and a sealing mechanism for a door to said chamber.

4. The device of claim 1 wherein all components of said steam generation system which are exposed to water or steam are comprised substantially of stainless steel.

5. The steam sterilizer device of claim 1 further including a temperature sensor to gauge fluid within said mixing tank and a valve on said outside water source controlled by said sensor to selectively flow outside water into said mixing tank.

6. The steam sterilizer device of claim 1 wherein said air break is further comprised of an upper section of tubing and a lower section of tubing, said lower section of tubing having a larger diameter than said upper section of tubing, said upper section at least partially enclosed within said lower section with a gap between said upper and lower sections providing access to an outside atmosphere.

7. The device of claim 1 wherein said mixing tank is in fluid communication with said reverse osmosis filter.

8. A steam sterilizer device including a sterilization chamber, a steam generation system including a steam generating apparatus and a filter and a discharge mixing tank, said mixing tank comprised of a reservoir having an inlet in fluid communication with an outlet to said chamber, an inlet in fluid communication with an outside water source, an inlet in fluid communication with said filter to recover a filtrate and an outlet in fluid communication with a discharge conduit.

9. The device of claim 7 including a temperature sensor to gauge fluid within said reservoir and a valve on said outside water source controlled by said sensor to selectively flow outside water into said reservoir to achieve a fluid temperature less than 140°.

10. The device of claim 8 wherein said filter is a reverse osmosis filter.

* * * * *